United States Patent [19]

Matsuno et al.

[11] Patent Number: 5,547,938
[45] Date of Patent: *Aug. 20, 1996

[54] THERAPEUTIC AGENT FOR DIGESTIVE TRACT DISEASES USING GLICENTIN

[75] Inventors: Seiki Matsuno; Iwao Sasaki; Akira Ohneda, all of Sendai; Kazuyuki Sasaki, Saitama-ken; Yohei Natori, Saitama-ken; Tomohisa Nagasaki, Saitama-ken, all of Japan

[73] Assignee: Nisshin Flour Milling Co., Ltd., Tokyo, Japan

[*] Notice: The term of this patent shall not extend beyond the expiration date of Pat. No. 5,432,156.

[21] Appl. No.: 377,833

[22] Filed: Jan. 25, 1995

Related U.S. Application Data

[63] Continuation of Ser. No. 193,863, Feb. 9, 1994, Pat. No. 5,432,156.

[30] Foreign Application Priority Data

Feb. 24, 1993 [JP] Japan .................................. 5-35266
Oct. 18, 1993 [JP] Japan ................................. 5-269799
Dec. 24, 1993 [JP] Japan ................................. 5-326698

[51] Int. Cl.⁶ .............................. C07K 7/34; A61K 38/26
[52] U.S. Cl. ............................................. 514/012; 514/21
[58] Field of Search ......................... 514/12, 21; 530/324

[56] References Cited

U.S. PATENT DOCUMENTS 5,432,156  7/1995  Matsuno et al. ........................ 514/12

FOREIGN PATENT DOCUMENTS 4364199  12/1992  Japan .

OTHER PUBLICATIONS

Nature 304, Bell et al, pp. 368–371 (1983).
Br. J. Surg., Sagor et al, pp. 14–18, vol. 6, (1982).
Gut 12, Gleeson et al, pp. 773–782, (1971).
Gut 13, Bloom, pp. 520–523 (1972).
Peptide 3, Uttenthal et al, p. 84 (1982).
S. N. 08/415,939 filed Apr. 2, 1995 (cited by applicant).

*Primary Examiner*—Howard E. Schain
*Attorney, Agent, or Firm*—Oblon, Spivak, McClelland, Maier, & Neustadt, P.C.

[57]  ABSTRACT

Therapeutic agents for the digestive tract diseases which comprise glicentin as active ingredients.

4 Claims, 2 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 69 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:1:

```
Arg Ser Leu Gln Asp Thr Glu Glu Lys Ser Arg Ser Phe Ser Ala Ser
 1               5                  10                  15

Gln Ala Asp Pro Leu Ser Asp Pro Asp Gln Met Asn Glu Asp Lys Arg
                20                  25                  30

His Ser Gln Gly Thr Phe Thr Ser Asp Tyr Ser Lys Tyr Leu Asp Ser
                35                  40                  45

Arg Arg Ala Gln Asp Phe Val Gln Trp Leu Met Asn Thr Lys Arg Asn
    50                  55                  60

Arg Asn Asn Ile Ala
65
```

( 2 ) INFORMATION FOR SEQ ID NO:2:

( i ) SEQUENCE CHARACTERISTICS:
        ( A ) LENGTH: 70 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:2:

```
Met Arg Ser Leu Gln Asp Thr Glu Glu Lys Ser Arg Ser Phe Ser Ala
```

```
        1                   5                           10                          15

Ser  Gln  Ala  Asp  Pro  Leu  Ser  Asp  Pro  Asp  Gln  Met  Asn  Glu  Asp  Lys
                   20                       25                       30

Arg  His  Ser  Gln  Gly  Thr  Phe  Thr  Ser  Asp  Tyr  Ser  Lys  Tyr  Leu  Asp
              35                       40                       45

Ser  Arg  Arg  Ala  Gln  Asp  Phe  Val  Gln  Trp  Leu  Met  Asn  Thr  Lys  Arg
         50                       55                       60

Asn  Arg  Asn  Asn  Ile  Ala
    65                       70
```

( 2 ) INFORMATION FOR SEQ ID NO:3:

( i ) SEQUENCE CHARACTERISTICS:
        ( A ) LENGTH: 207 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:3:

```
CGTTCCCTGC  AGGACACTGA  AGAAAAATCT  CGTTCTTTCT  CTGCTTCTCA  GGCTGACCCA      60

CTGTCGGATC  CAGACCAGAT  GAACGAAGAC  AAACGTCATT  CTCAGGGTAC  TTTCACTTCT     120

GACTACTCTA  AATACCTGGA  CTCTCGTCGA  GCTCAGGACT  TCGTTCAGTG  GCTGATGAAC     180

ACTAAACGTA  ACCGTAACAA  CATCGCC                                            207
```

THERAPEUTIC AGENT FOR DIGESTIVE TRACT DISEASES USING GLICENTIN

This is a Continuation of application Ser. No. 08/193,863 filed on Feb. 9, 1994, now U.S. Pat. No. 5,432,156.

FIELD OF THE INVENTION

This invention relates to therapeutic agents for digestive tract diseases, comprising glicentin as an active ingredient and also to the use of glicentin as therapeutic agents for digestive tract-diseases by administering glicentin to a patient to promote proliferation of digestive tract mucosa. It is also concerned with the use of glicentin as therapeutic agents for digestive tract diseases by delayed migration of contents in the digestive tract to achieve improved gastrointestinal motor symptoms or to promote cure of the same.

BACKGROUND OF THE INVENTION

Glicentin which is one of enteroglucagons is a peptide comprising 69 amino acid residues. For example, human glicentin is composed of the following amino acid sequence (SEQ ID NO:1)

Arg-Ser-heu-Gln-Asp-Thr-Glu-Glu-Lys-Ser-Arg-Ser-Phe-Ser-Ala-Ser-Gln- Ala- Asp-Pro-Leu-Ser-Asp-Pro-Asp-Gln-Met-Asn-Glu-Asp-Lys-Arg-His-Ser- Gln-Gly-Thr-Phe-Thr-Ser-Asp-Tyr-Ser-Lys-Tyr-Leu-Asp-Ser-Arg-Arg-Ala- Gln-Asp-Phe-Val-Gln-Trp-Leu-Met-Asn-Thr-Lys-Arg-Asn-Arg-Asn-Asn-Ile-Ala The sequence contains in positions 33-61 the structure of glucagon which is a peptide hormone comprising 29 amino acid residues. Glicentin and glucagon are produced by tissue specific processing from the same precursor, preproglucagon. Glucagon is formed in pancreas and glicentin in intestine. Regarding physiological roles of these peptides, glucagon is known to control glycogenolysis and blood glucose level. However, the role is unknown for glicentin.

Glucagon-producing tumors are a very rare disease. One case was reported by Gleeson et al. in Gut, 12, 773–782, 1971, which was characterized by symptoms in small intestinal structure and function such as thickened small intestinal villi, delayed passing rate of food through the digestive tract and constipation. These findings and symptoms were found to have disappeared after removal of the tumor by surgical operation, possibility for factors produced by the tumor to participate in the altered small intestinal structure and function was postulated. Later, it was discovered by Bloom in Gut, 13, 520–523, 1972 that the tumor produced enteroglucagon. It was thus suggested that such symptoms were due to biological activity of enteroglucagon. It was further observed in animal experiments that jejunectomy brought about an increase in blood enteroglucagon level and a promoted productivity of cryptocell, by which the proliferating effect of enteroglucagon on epithelial cells of the intestinal tract was supported (Brit. g. Surg., 69, 14–18, 1982). It is however uncertain whether enteroglucagon as a trophic factor brings about proliferation of the small intestinal mucosa or both the increase in blood level and the mucosal proliferation are due to other factors. In addition, it was reported that a crude extract of enteroglucagon stimulated DNA synthesis in cultured cells of the small intestine (O. Ottenthal et al., Regul. Pept., 3, 84, 1982). However, it is uncertain whether the action is due to enteroglucagon itself, particularly glicentin, because its sample contains many impurities.

Enteroglucagon is also called gut glucagon-like immunoreactivity, which is defined on the basis of immunoreactivity against anti-glucagon antiserum of low specificity and contains a number of peptides produced by tissue specific processing from the same preproglucagon. A plural of candidates are presented as the active form in blood, including oxyntomodulin, i.e., a peptide hormone in positions 33–69 of the amino acid sequence of glicentin, glucagon 1–21, i.e., a peptide in positions 33–53, glucagon-like peptide-1, i.e., a peptide hormone which occurs in a region of preproglucagon containing no glicentin and similar glucagon-like peptide-2. Thus, the role of glicentin, a kind of enteroglucagon has not yet been elucidated and also its target tissue and cell are unclear. Moreover, human glicentin has neither been isolated nor studied as a substance.

The present inventors were successful in synthesizing DNA corresponding to the amino acid sequence of human glicentin which was deduced by G. I. Bell (Nature, 304, 368–371 (1983)) from the sequence of human preproglucagon gene and preparing human glicentin by means of genetic engineering procedure using the synthesized DNA (Japanese Patent Kokai Hei 4-364199). Thus, human glicentin has easily been made available in a large amount and as a purified product.

The intestinal tract is an organ mainly participating in digestion of food and absorption of nutritional elements. Ingestion of the nutritional elements necessary for life conservation is mostly effected via the intraluminal mucosal layer of the intestinal tract. It is therefore a serious problem to the living body to have the functions of the digestive tract impaired by histological atrophy, development of ulcers or reduction in function of the mucosa after pathological or surgical injuries, and further, to have permeability of the intestinal mucosa abnormally intensified to allow for translocation of bacteria or foreign bodies. Thus, when a digestive tract is invaded or atrophied, rapid cure and recovery of function of the digestive tract are desirable. In case of the hypoplasia of the digestive tract tissues, it is necessary to promote their growth and enhance their function.

It is also known that atrophy of the intestinal mucosa occurs by exposure to strong radiation or other cytostatic stimulus because turnover of the intestinal mucosal cells is very rapid. Furthermore, it is known that atrophy of the intestinal mocosa occurs also by adopting intravenous or parenteral nutrition which does not require intestinal functioning, or enteral nutrition or elemental diet which does not require normal digestive tract functions, when functions of the intestinal tract are reduced, or digestion and absorption in the intestinal tract fail after the intestinal tract operation. However, no drug is present which induces proliferation of the cells of intestinal mucosa for the treatment of functional disorder of the digestive tract caused by atrophy of the digestive tract mucosa. Therefore, there is a continuing desire to develop such drug.

Further, diseases associated with resection of digestive tract, e.g., damping syndrome associated with an extensive gastrectomy bring about abnormally accelerated excretion of the intragastric contents, thus leading to rapid migration of not completely digested food to the jejunum, which results in hypertonicity of the contents in the jejunum. This will induce various pathological conditions such as sweating, tachycardia and nausea. Short gut syndrome caused by extensive resection of the intestinal tract in the treatment of various diseases or reduction in function of the small intestine is accompanied by exaggerated secretion of gastric acid, exaggerated peristalsis of the stomach and other reactions. These reactions occur as a result of failure of the feedback mechanism due to lack of the cells in the digestive tract mucosa that produce digestive tract hormones, physiologically active peptides and the like.

SUMMARY OF THE INVENTION

The present inventors have found that human glicentin has an activity of proliferating an intestinal mucosa and also inhibits a peristalsis of the stomach, and have elucidated that glicentin is useful as a therapeutic agent for digestive tract diseases, thus leading to the present invention.

The present invention provides a therapeutic agent for digestive tract diseases, which comprises glicentin as an active ingredient.

The term "digestive tract" as used herein means a tube through which food passes, including stomach and intestine. The term "digestive tract diseases" as used herein means diseases accompanied by a qualitative or quantitative abnormality in the digestive tract mucosa, which include, e. g., ulceric or inflammatory disease; congenital or acquired digestion and absorption disorder including malabsorption syndrome; disease caused by loss of a mucosal barrier function of the gut; and protein-losing gastroenteropathy. The ulceric disease includes, e.g., gastric ulcer, duodenal ulcer, small intestinal ulcer, colonic ulcer and rectal ulcer. The inflammatory disease include, e.g. , esophagitis, gastritis, duodenitis, enteritis, colitis, Crohn's disease, proctitis, gastrointestinal Behcet, radiation enteritis, radiation colitis, radiation proctitis, enteritis and medicamentosa. The malabsorption syndrome includes the essential malabsorption syndrome such as disaccharide-decomposing enzyme deficiency, glucose-galactose malabsorption, fructose malabsorption; secondary malabsorption syndrome, e.g., the disorder caused by a mucosal atrophy in the digestive tract through the intravenous or parenteral nutrition or elemental diet, the disease caused by the resection and shunt of the small intestine such as short gut syndrome, cul-de-sac syndrome; and indigestible malabsorption syndrome such as the disease caused by resection of the stomach, e.g., dumping syndrome.

The term "therapeutic agent for digestive tract diseases" as used herein means the agents for the prevention and treatment of the digestive tract diseases, which include, e.g., the therapeutic agent for digestive tract ulcer, the therapeutic agent for inflammatory digestive tract disease, the therapeutic agent for mucosal atrophy in the digestive tract and the therapeutic agent for digestive tract wound, the amelioration agent for the function of the digestive tract including the agent for recovery of the mucosal barrier function and the amelioration agent for digestive and absorptive function.

The ulcers include digestive ulcers and erosions, acute ulcers, namely, acute mucosal lesions. Glicentin of the present invention, because of promoting proliferation of intestinal mucosa, can be used in the treatment and prevention of pathologic conditions of insufficiency in digestion and absorption, that is, treatment and prevention of mucosal atrophy, or treatment of hypoplasia of the digestive tract tissues and decrease in these tissues by surgical removal as well as improvement of digestion and absorption. Further, glicentin can be used in the treatment of pathologic mucosal conditions due to inflammatory diseases such as enteritis, Crohn's disease and ulceric colitis and also in the treatment of reduction in function of the digestive tract after operation, for example, in damping syndrome as well as in the treatment of duodenal ulcer in conjunction with the inhibition of peristalsis of the stomach and rapid migration of food from the stomach to the jejunum. Furthermore, glicentin can effectively be used in promoting cure of surgical invasion as well as in improving functions of the digestive tract. Thus, the present invention also provides a therapeutic agent for atrophy of the digestive tract mucosa, a therapeutic agent for wounds in the digestive tract and a drug for improving functions of the digestive tract which comprise glicentin as active ingredients.

DETAILED DESCRIPTION OF THE INVENTION

Figure 1:
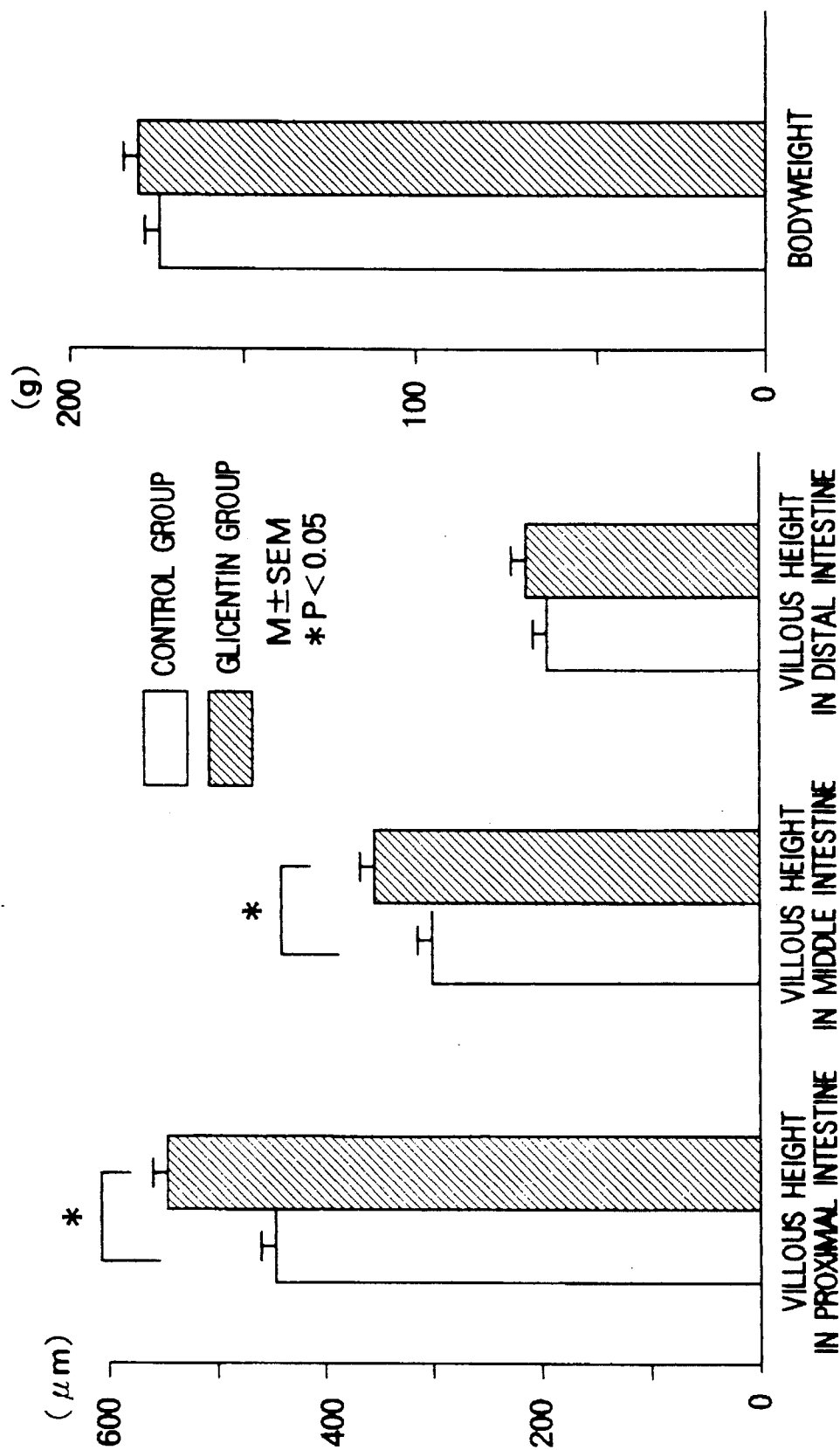
FIG. 1 is a figure showing increase in length of intestinal villi by the administration of glicentin.

In the present invention, an administration of glicentin promotes proliferation of the digestive tract mucosa, which leads to the treatment and prophylaxis of functional disorder of the digestive tract induced by atrophy or reduction of the digestive tract mucosa.

Furthermore, glicentin, which inhibits peristalsis of the stomach and rapid migration of food to the small intestine, is also used in the treatment of reduction in function of the digestive tract after operation or the treatment of duodenal ulcer.

Glicentin which can be used in the present invention includes any glicentin of an animal origin such as human, porcine, bovine, hamster, rat and guinea pig, as well as glicentin containing additional methionine (Met) at the N-terminus, which are prepared by a genetic engineering procedure or a synthetic process. Preferably, human glicentin is used in view of an undesirable allergic reaction or the like produced when being administered to humans. More preferably, there is used human glicentin (natural type) not containing additional methionine (Met) at the N-terminus.

Human glicentin (natural type) has the following amino acid sequence: (SEQ ID NO:1)

Arg-Ser-Leu-Gln-Asp-Thr-Glu-Glu-Lys-Ser-Arg-Ser-Phe-Ser-Ala-Ser-Gln- Ala-Asp-Pro-Leu-Ser-Asp-Pro-Asp-Gln-Met-Asn-Glu-Asp-Lys-Arg-His-Ser- Gln-Gly-Thr-Phe-Thr-Ser-Asp-Tyr-Ser-Lys-Tyr-Leu-Asp-Ser-Arg-Arg-Ala- Gln-Asp-Phe-Val-Gln-Trp-Leu-Met-Asn-Thr-Lys-Arg-Asn-Arg-Asn-Asn-Ile-Ala

Further, human glicentin containing additional methionine (Met) at the N-terminus has the following amino acid sequence: (SEQ ID NO:2)

Met-Arg-Ser-Leu-Gln-Arg-Thr-Gln-Glu-Lys-Ser-Arg-Ser-Phe-Ser-Ala-Ser- Gln-Ala-Asp-Pro-Leu-Ser-Asp-Pro-Asp-Gln-Met-Ash-Glu-Asp-Lys-Arg-His- Ser-Gln-Gly-Thr-Phe-Thr-Ser-Asp-Tyr-Ser-Lys-Tyr-Leu-Asp-Ser-Arg-Arg- Ala-Gln-Asp-Phe-Val-Gln-Trp-Leu-Met-Asn-Thr-Lys-Arg-Asn-Arg-Asn-Asn-Ile-Ala

The above human glicentin can be prepared by a genetic engineering procedure or a synthetic process from a gene of the DNA sequence corresponding to the above amino acid sequence. An example of the genetic engineering procedure is a process of producing a desired human glicentin which comprises preparing a synthetic gene encoding human glicentin amino acid sequence of the following DNA sequence (SEQ ID NO:3) which has been suggested by the present inventors in Japanese Patent Kokai Hei 4-364199, introducing the synthetic gene into plasmid, transforming *E. coli* with the resultant plasmid and culturing the transformant.

```
5' CGTTCC CTGCAGGACA CTGAAGAAAA ATCTCGT-
   TCT TTCTCTGCTT CTCGGCTGA
3' GCAAGG GACGTCCTGT GACTTCTTTT TAGAG-
   CAAGA AAGAGACGAA GAGTCCGACT
   CCCACTGTCG GATCCAGACC AGATGAACGA AGA-
   CAAACGT CATTCTCAGG GTACTTTCAC
   GGGTGACAGC CTAGGTCTGG TCTACTTGCT TCT-
   GTTTGCA GTAAGAGTCC CATGAAAGTG
   TTCTGACTAC   TCTAAATACC   TGGACTCTCG
   TCGAGCTCAG GACTTCGTTC AGTGGCTGAT
   AAGACTGATG   AGATTTATGG   ACCTGAGAGC
   AGCTCGAGTC CTGAAGCAAG TCACCGACTA
   GAACACTAAA CGTAACCGTA ACAACATCGC C 3'
   CTTGTGATTT GCATTGGCAT TGTTGTAGCG G 5'
```

Other processes of producing the human glicentin include introducing into plasmid a gene of another DNA sequence corresponding to the above amino acid sequence of glicentin, transforming E. coli, Bacillus subtilis, yeast or other microorganism with the resultant plasmid and culturing the transformant or alternatively culturing a human glicentin productive cell. However, it should be understood that human glicentin used in the invention is not limited to one produced by the specific process and any human glicentin can be employed in the invention so far as it has the above amino acid sequence.

Usually, glicentin as the active ingredient can be administered orally or parenterally in the form of suitable pharmaceutical preparations. Such pharmaceutical preparations can be formulated in a conventional manner using one or more pharmaceutically acceptable vehicles, adjuvants and additives, e.g., binders, diluents, solubilizers, stabilizers, buffers, lubricants, coating agents, antioxidants, sweeteners, flavors, colorants and the like. Suitable preparations include powders, granules, tablets, capsules, injections, syrups, suspensions, emulsions or the like. If necessary, the active ingredient may be administered in combination with other drugs such as antacid, muscarine receptor antagonist and prostaglandin. It may be in bilayered or multilayered tablet with other drugs. The tablets may also be coated with a conventional coating to form, e.g., sugar-coated, enteric-coated or film-coated tablets.

In the formulation of solid preparations such as tablets and capsules, there may be used suitable additives such as lactose, refined sugar, crystalline cellulose, corn starch, calcium phosphate, sorbitol, carboxymethylcellutose, gum arabic, polyvinylpyrrolidone, hydroxypropylcellulose, glycerin, polyethylene glycol, stearic acid, magnesium stearate and talc. In the formulation of liquid preparations such as injections and syrups, suitable additives may be used such as sodium chloride, sorbitol, glycerin, olive oil, propylene glycol and ethyl alcohol.

For a preferred unit dosage form for oral administration, for instance, the aqueous or oily solutions, suspensions or emulsions may contain glicentin in an amount of 0.01 to 10 mg, advantageously 0.1 to 1 mg per 5 ml and the tablets, capsules or granules may contain glicentin in an amount of 0.01 to 10 mg, advantageously 0.1 to 1 mg.

From the chemical structure, glicentin is considered to undergo a denaturation by an acid within intestine, a decomposition by digestion and a reduction in activity by such denaturation, when administered orally to human body. Therefore, it is recommendable to release the active ingredient, glicentin within intestine using an enteric coating. Thus the active ingredient is preferably coated with a conventional enteric coating agent in the oral administration. The enteric coating agents include synthetic polymers such as EUDRAGI®, polyacrylate base (available from Rohm Pharma), semisynthetic polymers such as cellulose acetate phthalate or the like.

A preferable administration of glicentin is parenteral for the reason of its not undergoing denaturation or decomposition. The parenteral administration includes subcutaneous, intravenous, intramuscular and intraperitoneal injections. Glicentin can be formulated into the aqueous or oily solutions, suspensions or emulsions. Preferably, glicentin is administered in the form of depot preparations for a prolonged effect of glicentin over a long period of time.

A dose of the active ingredient can be varied depending on the route of administration, the symptoms, age, sex and weight of patients and other factors, but suitably can be in the range so as to provide a level of 100 pM to 10,000 pM in blood. Usual parenteral dosage for adult human ranges from 0.5 µg/kg to 500 µg/kg. However, lower or higher amount may be administered within the safety range.

When 10 mg/kg of human glicentin (natural type) is intraperitoneally administered to male BALB/c mice (6 weeks age), no change in appearance is observed.

The present invention is further illustrated by the following examples. The numerical values in the tables are shown by average value ± standard error.

EXAMPLE 1

An experiment was performed in male SD rats weighing 140–160 g which had been fed on standard food under light-dark condition of a cycle of 12 hours. The food which was replaced by an elemental nutrition (Elental®, Morishita-Roussel Japan) was taken ad lib., and remained unchanged until the experiment was finished. After feeding on the component nutrition for 3 days, administration of glicentin prepared as described below was started.

Gelatin was dissolved in warm water to a weight ratio of 16%, and the solution autoclaved and cooled to room temperature. To 40 ml of the gelatin solution was added a solution of 1 mg of glicentin in 10 ml of distilled water with stirring at room temperature. The mixture was divided into test tubes, freeze dried and stored for use.

The gelatin solution was subcutaneously given at a dose of 10 µg per glicentin every 12 hours for 7 days to examine a nutritional effect of glicentin on the intestinal mucosae. A similar gelatin solution containing no glicentin was given for the same period of time as a control for comparison. Twelve hours after completion of the final administration, the rats were sacrificed and subjected to removal of the small intestine in the region from the Treitz's ligamentum to the cecum. The removed small intestine was cut at the central site to separate it into the jejunum and the ileum. The lumen of each of the intestinal tracts was gently washed with an aqueous physiological saline solution. The intestinal tracts were longitudinally incised, respectively, and tissues were removed of a portion of the jejunum in proximity to the duodenum, a portion of the ileum in proximity to the cecum and a portion around the boundary between the jejunum and the ileum and fixed in a 3.7% formalin solution as the proximal, distal and middle sites of the small intestine, respectively. Mucosae were collected by ablation with a spatula from the remainder of the intestinal tracts and weighed, respectively. The results are shown in Table 1.

The tissues fixed in the formalin solution were embedded in paraffin to form a preparation which was stained with hematoxylin-eosin and measured for height of the villi using an optical microscope. The results are shown in Table 2.

TABLE 1

|  | Control group | Glicentin group |
|---|---|---|
| Bodyweight | | |
| before administration | 146.3 ± 2.9 | 161.0 ± 10.4 |
| after administration | 174.4 ± 40 | 180.8 ± 5.3 |
| Length of small intestine, cm | 103.8 ± 1.3 | 107.0 ± 4.8 |
| Length of small intestine, cm/ 100 g bodyweight | 71.1 ± 1.6 | 66.4 ± 1.7 |
| Jejunal mucosal weight, g | 0.97 ± 0.06 | 1.3 ± 0.12 |
| Jejunal mucosal weight, g/ 100 g bodyweight | 0.56 ± 0.04 | 0.75 ± 0.08 |
| Ileal mucosal weight, g | 0.94 ± 0.06 | 1.04 ± 0.09 |
| Ileal mucosal weight, g/ 100 g bodyweight | 0.54 ± 0.03 | 0.57 ± 0.04 |
| Whole small intestinal mucosal weight, g | 1.92 ± 0.07 | 2.38 ± 0.12 |
| Whole small intestinal mucosal weight, g/100 g bodyweight | 1.10 ± 0.04 | 1.32 ± 0.03 |

TABLE 2

|  | Control group | Glicentin group |
|---|---|---|
| Villous height in proximal intestine, μm | 447 ± 13.2 | 546 ± 18.6 |
| Villous height in middle intestine, μm | 301 ± 12.3 | 354 ± 7.5 |
| Villous height in distal intestine, μm | 200 ± 12.4 | 216 ± 8.4 |

Effects of the administration of glicentin on increases in intestinal villous height and in bodyweight in comparison with those in the control group are graphically shown in FIG. 1.

The experimental results indicate that glicentin significantly increases the jejunal mucosal weight and the whole small intestinal mucosal weight including jejunum and ileum. There was also shown a tendency to increase ileal mucosa and length of the small intestine. These experimental results indicate that glicentin has a trophic effect on intestinal mucosa.

EXAMPLE 2

A solution of glicentin dissolved in a small amount of distilled water for injection was diluted with a 2% solution of bovine albumin prepared with a physiological saline solution for injection to a concentration of 400 μg/ml (50 nmol/ml). The solution was frozen and stored until used. On use it was 1:10 diluted with the physiological saline solution and subcutaneously given to rats at a dose of 0.2 ml, i.e., 1 nmol of glicentin per rat.

As control were used GRPP which was a peptide in positions 1–30 of the amino acid sequence of glicentin, oxyntomodulin, glucagon, glucagon 1–21 and glucagon-like peptide-1. They were prepared and administered in the same way as glicentin at a dose of 1 nmol. Glucagon was purchased from Novonordisk Co., Ltd. The other control peptides were synthesized using BIOLYNX, a peptide synthesizer manufactured by LKB Co., Ltd. A physiological saline solution for injection was administered as a control group.

The rats were sacrificed, and the small intestine was removed in the same way as in Example 1. The small intestine was divided equally into four parts and the third part from the duodenum was measured for the weight of the mucosa. The results are shown in Table 3.

These results indicate that only glicentin significantly increases the weight of intestinal mucosa unlike GRPP, oxyntomodulin, glucagon, glucagon 1–21 and glucagon-like peptide-1.

TABLE 3

|  | Intestinal mucosal weight (mg) |
|---|---|
| Control goup | 0.498 ± 0.038 |
| Glicentin group | 0.614 ± 0.025* |
| GRPP group | 0.491 ± 0.046 |
| Oxyntomodulin group | 0.506 ± 0.046 |
| Glucagon | 0.532 ± 0.040 |
| Glucagon 1–21 | 0.490 ± 0.048 |
| Glucagon-like peptide-1 | 0.498 ± 0.042 |

*$p > 0.05$

EXAMPLE 3

An experiment was performed as described below in order to examine the action of glicentin on a motility of the digestive tracts after meal.

Six hybrid dogs weighing 16–18 kg were sutured with strain gauge transducers (manufactured by Star Medical, F121S) at a site of the gastric antrum 4 cm from the pyloric ring, a site of the duodenum for the main incurrent pancreatic duct and a site of the jejunum 10 cm from the Treitz's ligamentum, respectively, to measure the contractile force intensity of the circular muscle. Recovery period for the suture was 2 weeks.

Three of the 6 dogs were intravenously given over 1 hour 15 ml of a physiological saline solution in which 400 pmol of glicentin had been dissolved per kg of bodyweight. The remaining three received an aqueous physiological solution containing no glicentin in the same way as above as a control for comparison. The dogs were fed on 15 g of a solid diet (SD®, manufactured by Oriental Yeast K. K.) and 15 g of Vitaone® (manufactured by Nihon Pet Food K. K. and Kyodo Shiryo K. K.) per kg of bodyweight simultaneously with the intravenous administration.

Figure 2:
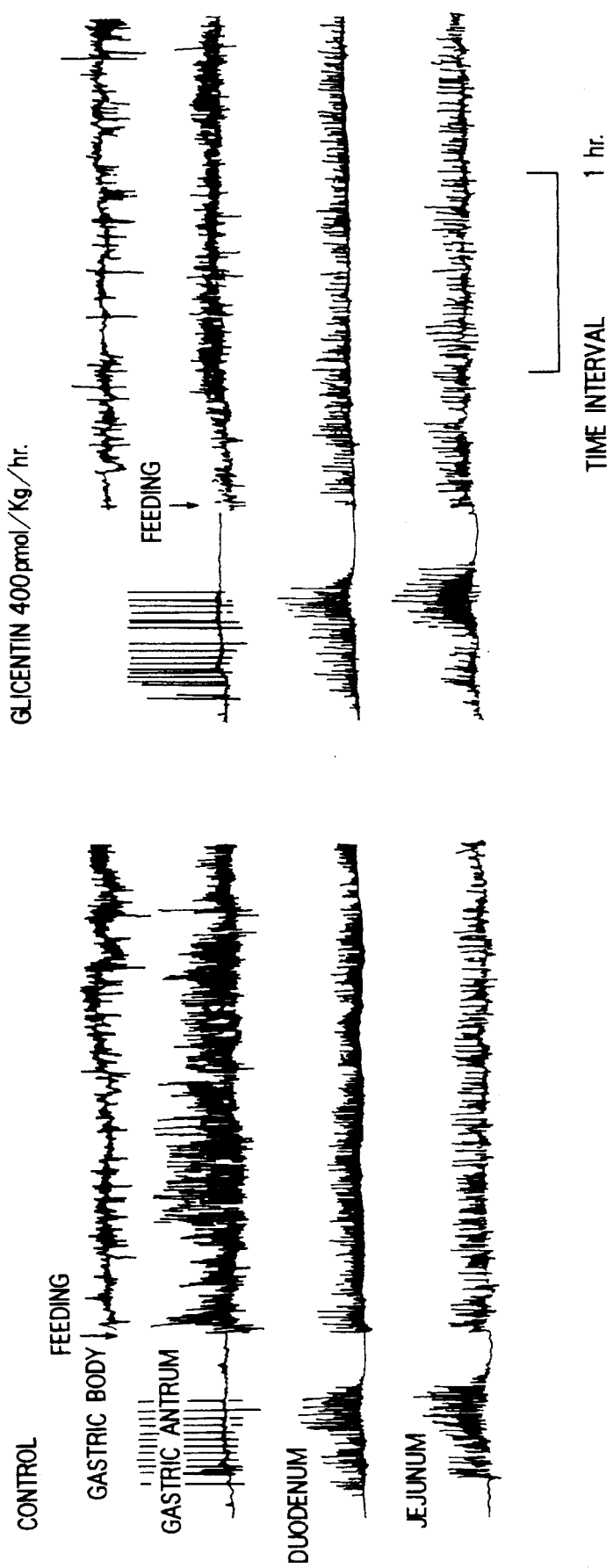
FIG. 2 is a figure showing the effect of glicentin on the motor activity in the digestive tract in the post-feed period.

Then, the motor activity of the digestive tracts and length of the post-feed period were measured. The results are shown in FIG. 2 and Table 3. Intensity of the contraction in the post-feed period was integrated for the two-hour measurements and evaluated in comparison with the mean level of the signal peak in phase 3 motor activity of the intestinal tracts in hunger and taken as a motor index. The results are shown in Table 5.

These experimental results indicate that glicentin had no influence upon the length of the post-feed period and inhibited the post-feed motility in the vestibulum of stomach, thus demonstrating an effectiveness of glicentin in the treatment of increased gastric peristalsis in damping syndrome or short gut syndrome caused by excision of the stomach or the intestinal tract.

TABLE 4

|  | Length of post-feed period (hr.) |
|---|---|
| Control group | 14.8 ± 0.3 |
| Glicentin group | 13.6 ± 1.0 |

TABLE 5

|  | Motor index | |
| --- | --- | --- |
|  | Control group | Glicentin group |
| Stomach vestibulum | 1.670 ± 0.2 | 0.878 ± 0.1 |
| Duodenum | 1.070 ± 0.1 | 0.675 ± 0.4 |
| Jejunum | 0.829 ± 0.2 | 1.087 ± 0.2 |

The results in Examples 1 and 3 indicate that glicentin promotes the proliferation of the intestinal mucosa, thus demonstrating the activity of proliferating the digestive tract mucosa. The results in Example 2 indicate that glicentin inhibits the peristalsis of the stomach, thereby to inhibit the sudden movement of food to the gut. Thus, glicentin is found useful as a therapeutic agent for digestive tract diseases.

The following examples illustrate the formulation of typical pharmaceutical preparations containing glicentin according to the invention.

Preparation 1

5 g of glicentin, 2 kg of lactose, 20 g of magnesium stearate and 100 g of corn starch were mixed, the mixture was compressed, the compressed mixture was pulverized to granules. The granules were formed in a tabletting machine to tablets each containing 50 µg of glicentin. The tablets were coated with cellulose acetate phthalate to form enteric-coated tablets.

Preparation 2

0.1 g of glicentin, 30 g of refined sugar, 26 g of 70% D-sorbitol, 0.03 g of ethyl p-oxybenzoate and 0.015 g of propyl p-oxybenzoate were dissolved in 60 g of warm water. After cooling, 0.15 g of glycerin and a solution of the flavor in 0.5 g of 96% ethanol were added. Water was added to the mixture to make up a total amount of 100 ml of syrup.

Preparation 3

1 g of glicentin and 99 g of lactose were mixed and the mixture was dissolved in 1 liter of distilled water for injection. The solution was filtered through a sterile filter (e.g., a 0.22 µm membrane filter), 1 ml portions of the filtered solution were dispensed into vial bottles under sterile condition and freeze dried to provide the preparations for injection. The preparations are dissolved in distilled water on use.

Preparation 4

5 g of glicentin, 400 g of lactose, 150 g of crystalline cellulose, 150 g of calcium stearate and 300 g of talc were mixed thoroughly, the mixture was compressed, the compressed mixture was pulverized to granules. The granules were encapsuled into two-piece capsules each containing 10.0 µg of glicentin.

---

What is claimed is:

1. A method for inhibiting peristalsis of the stomach or duodenum comprising:

administering an effective amount of glicentin to a subject in need of inhibition of peristalsis of the stomach or duodenum.

2. The method of claim 1, wherein glicentin is human glicentin.

3. The method of claim 1, wherein glicentin has the amino acid sequence:

Arg-Ser-Leu-Gln-Asp-Thr-Glu-Glu-Lys-Ser-Arg-Ser-Phe-Ser-Ala-Ser-Gln- Ala-Asp-Pro-Leu-Ser-Asp-Pro-Asp-Gln-Met-Asn-Glu-Asp-Lys-Arg-His-Ser- Gln-Gly-Thr-Phe-Thr-Ser-Asp-Tyr-Ser-Lys-Tyr-Leu-Asp-Ser-Arg-Arg-Ala- Gln-Asp-Phe-Val-Gln-Trp-Leu-Met-Asn-Thr-Lys-Arg-Asn-Arg-Asn-Asn-Ile-Ala (SEQ ID NO:1).

4. The method of claim 1, wherein glicentin has the amino acid sequence:

Met-Arg-Ser-Leu-Gln-Asp-Thr-Glu-Glu-Lys-Ser-Arg-Ser-Phe-Ser-Ala-Ser- Gln-Ala-Asp-Pro-Leu-Ser-Asp-Pro-Asp-Gln-Met-Asn-Glu-Asp-Lys-Arg-His- Ser-Gln-Gly-Thr-Phe-Thr-Ser-Asp-Tyr-Ser-Lys-Tyr-Leu-Asp-Ser-Arg-Arg- Ala-Gln-Asp-Phe-Val-Gln-Trp-Leu-Met-Asn-Thr-Lys-Arg-Asn-Arg-Asn-Asn-Ile-Ala (SEQ ID NO:2).

\* \* \* \* \*

UNITED STATES PATENT AND TRADEMARK OFFICE
CERTIFICATE OF CORRECTION

PATENT NO. : 5,547,938
DATED : August 20, 1996
INVENTOR(S) : Seiki MATSUNO, ET AL.

It is certified that error appears in the above-indentified patent and that said Letters Patent is hereby corrected as shown below:

On the title page, Item [30], The Foreign Application Priority Data should read:

```
-- [30]  Feb. 24, 1993  [JP]  Japan.......5-35266
         Oct. 18, 1993  [JP]  Japan.......5-259799
         Dec. 24, 1993  [JP]  Japan.......5-326698--
```

Signed and Sealed this

Third Day of December, 1996

Attest:

BRUCE LEHMAN

Attesting Officer     Commissioner of Patents and Trademarks